(12) United States Patent
Fujihara et al.

(10) Patent No.: US 7,517,646 B2
(45) Date of Patent: Apr. 14, 2009

(54) FUNCTIONAL MOLECULE AND PROCESS FOR PRODUCING THE SAME

(75) Inventors: Tsuyoshi Fujihara, Kawasaki (JP); Shozo Fujita, Kawasaki (JP); Shunsaku Takeishi, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 497 days.

(21) Appl. No.: 10/943,150

(22) Filed: Sep. 17, 2004

(65) Prior Publication Data
US 2005/0130195 A1    Jun. 16, 2005

Related U.S. Application Data

(63) Continuation of application No. PCT/JP03/03087, filed on Mar. 14, 2003.

(30) Foreign Application Priority Data

Mar. 19, 2002 (JP) ............................. 2002-077040

(51) Int. Cl.
*C12Q 1/68* (2006.01)
*C12P 19/34* (2006.01)
*C07H 21/00* (2006.01)
*C07H 21/02* (2006.01)
*C07H 19/04* (2006.01)

(52) U.S. Cl. ................... 435/6; 435/91.1; 536/23.1; 536/25.3; 536/26.6

(58) Field of Classification Search .............. 435/6, 435/91.1; 536/23.1, 25.3, 26.6
See application file for complete search history.

(56) References Cited

U.S. PATENT DOCUMENTS
5,756,291 A    5/1998   Griffin et al.
(Continued)

FOREIGN PATENT DOCUMENTS
EP       0 544 809 B1    12/1998
(Continued)

OTHER PUBLICATIONS

Y. Lin, et al.; "High-affinity and specific recognition of human thyroid stimulating hormone (hTSH) by in vitro-selected 2'-amino-modified RNA"; *Nucleic Acids Research*; vol. 24; No. 17; 1996; pp. 3407-3414./Cited in the International search Report.
(Continued)

*Primary Examiner*—Jezia Riley
(74) *Attorney, Agent, or Firm*—Kratz, Quintos & Hanson, LLP (57) ABSTRACT

A process for producing a functional molecule includes a forming step which forms a modified nucleotide n-mer (where, n represents an integer) containing a modified nucleoside prepared by introducing a substituent into a nucleoside composing a nucleic acid; and a producing step which produces a modified oligonucleotide sequence by randomly polymerizing the modified nucleotide n-mer. A preferable embodiment thereof includes a selecting step which selects a sequence having an affinity to a target from the modified oligonucleotide sequence, a determining step which amplifies the selected modified oligonucleotide sequence and determines the base sequence thereof, and a translating step which translates the sequence of the modified oligonucleotide sequence on the basis of a relation table prepared by relating at least one of $4^n$ kinds of nucleotide n-mers, which are presented in the relation table prepared by the one-to-one combination of 4 kinds of nucleosides, to a modified nucleotide n-mer.

25 Claims, 3 Drawing Sheets

RELATION TABLE

| 5' \ 3' | A | C | G | T |
|---|---|---|---|---|
| A | ✕ | $C_2A$ | ✕ | $U_3A$ |
| C | $AC_1$ | $C_3C$ | $GC_6$ | $U_4C$ |
| G | ✕ | $C_4G$ | ✕ | $U_5G$ |
| T | $AU_1$ | $C_5T$ | $GU_2$ | $U_6T$ |

U.S. PATENT DOCUMENTS

| | | | |
|---|---|---|---|
| 6,423,493 B1 * | 7/2002 | Gorenstein et al. | 435/6 |
| 2002/0106679 A1 | 8/2002 | Taira et al. | |

FOREIGN PATENT DOCUMENTS

| | | |
|---|---|---|
| EP | 1 201 751 A1 | 5/2002 |
| JP | 6-503809 | 4/1994 |
| JP | 11-507529 | 7/1999 |
| JP | 2001-521040 | 11/2001 |
| JP | 2002-125685 | 5/2002 |
| JP | 2002-291491 | 10/2002 |
| WO | WO 92/05285 | 4/1992 |
| WO | WO 92/14842 | 9/1992 |
| WO | WO 96/40717 A1 | 12/1996 |
| WO | WO 99/21873 A2 | 5/1999 |
| WO | WO 00/23456 | 4/2000 |
| WO | WO 00/24404 | 5/2000 |

OTHER PUBLICATIONS

Supplementary Partial European Search Report dated Jul. 16, 2007.

W. Kusser; "Chemically Modified Nucleic Acid Aptamers for in Vitro Selections: Evolving Evolution"; Reviews in Molecular Biotechnology, Elsevier, Amsterdam, NL, vol. 74, No. 1, pp. 27-38, Mar. 2000; XP008042698.

K. Sakthivel et al; "Expanding the Potential of DNA for Binding and Catalysis: Highly Functionalized dUTP Derivatives That Are Substrates for Thermostable DNA Polymerases"; Angewandte Chemie. International Edition, Wiley VCH Verlag, Weinheim, DE, vol. 37, No. 20, pp. 2872-2875, Nov. 2, 1998; XP-002175620.

J. A. Latham et al; "The Application of a Modified Nucleotide in Aptamer Selection: Novel Thrombin Aptamers Containing 5-(1-pentynyl)-2'-deoxyuridine"; Nucleic Acids Research, Oxford University Press; Surrey, GB; vol. 22, No. 14; pp. 2817-2822; 1994; XP-002176163.

E. N. Brody et al; "The Use of Aptamers in Large Arrays for Molecular Diagnostics"; Molecular Diagnosis, Naperville, IL, US, vol. 4, No. 4; pp. 381-388; Dec. 1999; XP 009000095.

B. A. Gilbert et al; "RNA Aptamers that Specifically Bind to a K Ras-Derived Farnesylated peptide"; Bioorganic & Medicinal Chemistry; vol. 5, No. 6, pp. 1115-1122; Jun. 1997; XP-002473667.

S. D. Jhaveri et al; "In Vitro Selection of RNA Aptamers to a Protein Target by Filter Immobilization"; Current Protocols in Molecular Biology / Edited by Frederick M. Ausubel . . . [et al.] May 2001; vol. Chapter 24, p. unit 24.3; May 2001; XP-002473668.

Supplementary European Search Report dated Apr. 7, 2008.

* cited by examiner

FIG. 3D SEQ ID NO: 1   DNA   ATGCTCTAGCCCCT

SEQ ID NO: 2   $AU_1GC_6U_4CU_3AGC_6C_3CC_5T$

RELATION TABLE

| 5'\3' | A | C | G | T |
|---|---|---|---|---|
| A | X | $C_2A$ | X | $U_3A$ |
| C | $AC_1$ | $C_3C$ | $GC_6$ | $U_4C$ |
| G | X | $C_4G$ | X | $U_5G$ |
| T | $AU_1$ | $C_5T$ | $GU_2$ | $U_6T$ |

FUNCTIONAL MOLECULE AND PROCESS FOR PRODUCING THE SAME

CROSS-REFERENCE TO RELATED APPLICATIONS

This is a continuation of Application PCT/JP03/03087 filed on Mar. 14, 2003.

BACKGROUND OF THE INVENTION

1. Field of the Invention

The present invention relates to a functional molecule that shows a high affinity to various targets (targeted material), is easily amplified and replicated, is suitable for a wide range of fields such as drugs, drug delivery, biosensors, regulation of gene expression amount, conquest of diseases caused by an abnormal gene, elucidation of the function of the protein into which a gene is translated and development of reaction catalysts, and particularly suitable for analysis of the protein, and relates to a process for producing the same.

2. Description of the Related Art

In 2002, a draft of human whole gene information was published and in 2003, perfect information thereof is in a schedule to be elucidated. As a result, a central interest of researchers and scientists has shifted to an analysis of a protein being a gene product by a gene. The analysis of the protein become naturally possible by a presence of a molecule having an affinity to individual proteins targeted. Many kinds of proteins targeted for the analysis are present in a cell and many of them have completely unknown amino acid sequence and structure thereof. Therefore, many kinds of molecules are required for the analysis of the proteins.

However, at present, no process effective for preparing or obtaining the molecule used for the protein analysis has been known. The most common process, which has been known so far and is applied for obtaining the molecule having the affinity to a specific protein, is a process to select an affinity antibody by using an animal immune system. However, in this process, use of an animal requires a large amount of the protein, more number of steps, and a high cost. In addition, although the affinity antibody obtained through selection by this process can be replicated by making it as a monoclonal antibody followed by maintaining the cell, it requires a high cost and cannot be improved. Further, there is a problem in that only an affinity antibody having an affinity to the identical target can be selected. Therefore, selecting and obtaining each affinity antibody having an affinity to all kinds of proteins present in the cell is very difficult.

Recently many studies are conducted on selection of a molecule having a specific function from a nucleotide random sequence to identify the molecule on the basis of gene information thereof. As the result, many reports describe molecules having an affinity to a specific target and RNAs catalyzing a specific reaction.

However, a compositional unit number of a nucleotide is 4 in both RNA and DNA and, thus, kinds of functional groups present in a polymer thereof are very limited to limit naturally functions thereof. In order to solve this problem, a study by using a modified nucleotide has been carried out. However determining that a molecule, in which a specific site has received selectively a certain nucleotide, is the molecule requires removing a natural nucleotide, which is corresponding to the modified nucleotide, from an experimental system. As the result, the compositional unit number of the nucleotide is 4+1−1=4 making a radical solution impossible. Further, RNA is enzymatically very unstable and, thus, an attempt to synthesize a molecule having the same function by using a DNA, which is enzymatically stable, has been failed. In these cases, a molecule having an affinity to a specific target is obtained by repeated operation of amplification and purification and, therefore, it is at present difficult to synthesize many kinds of molecules.

On the other hand, in a study by using amino acid or an artificial material as a compositional unit to select the molecular by combinatorial chemistry, gene information, which is not contained in the molecule itself composed of the compositional unit, does not allow amplifying the sequence information. Therefore, determining the sequence of the molecule requires many steps.

Meanwhile, concerning the synthesis of the protein having the gene information, there is the study in which puromycin was introduced to a 3' terminal of an mRNA (e.g., refer to Japanese Patent Application Laid-Open (JP-A) No. 2002-291491). This study was carried out by applying the property that puromycin is misunderstood as the amino acid in a translation system and apt to be incorporated easily in the protein. However, in this case, so far, an efficiency of puromycin incorporation is very low and, hence, there is only a report describing that the molecule was selected from a library of a random 3 residues of amino acids. Moreover, there is the problem in that even if the efficiency of puromycin incorporation is improved, the number of a library pool possible finally to become the protein having the gene information in a DNA random pool is very small. Such problem arises from the fact that a termination codon is present on a DNA random sequence in a proportion of 3/64 and a rare codon which is not preferred by the cell is present.

SUMMARY OF THE INVENTION

The present invention has a purpose to provide a functional molecule having an affinity and specificity to a target comparable to the affinity and specificity of an antibody against an antigen, capable of functioning as similar to the antibody sensu stricto, capable of recognizing a wide range of targets, showing a high affinity to various kinds of targets (target material, detection target), easy to be amplified and replicated, preferably applicable in a wide range of fields such as drugs, drug delivery, biosensors, regulation of gene expression amount, conquest of diseases caused by an abnormal gene, elucidating the function of the protein into which a gene is translated and development of reaction catalysts, and preferable particularly for an analysis of a protein.

The present invention has the purpose to provide a process for producing a functional molecule unnecessary of repeated complicated operations of amplification and purification of the functional molecule and capable of producing effectively and integrally.

A process for producing a functional molecule according to the present invention includes a forming step which forms a modified nucleotide n-mer (where, n represents an integer) containing a modified nucleoside prepared by introducing a substituent into a nucleoside composing a nucleic acid; and a producing step which produces a modified oligonucleotide sequence by randomly polymerizing the modified nucleotide n-mer. According to the process for producing the functional molecule of the present invention, in the producing step, a modified oligonucleotide sequence is produced by polymerizing randomly a modified nucleotide n-mer (n representing the integer) containing a modified nucleoside prepared by inserting a substituent into the nucleoside composing the nucleic acid. The modified oligonucleotide sequence has more substituent numbers recognizing a target in comparison with 4 nucleotides composing the nucleic acid, holds a self-replicating ability of the nucleic acid as it is and is comparable to the antibody in the affinity and specificity. Therefore, amplifying and replicating the modified oligonucleotide sequence enables the efficient produce of various kinds of the functional molecule that can recognize the target.

The functional molecule according to the present invention is produced by the process for producing a functional molecule according to the present invention. In the functional molecule, the affinity and specificity to the target is comparable to the affinity and specificity of an antibody to an antigen, can recognize various kinds of targets, and is preferably usable for a wide range of fields such as drugs, drug delivery, biosensors, regulation of gene expression amount, conquest of diseases caused by gene abnormality and elucidation of the function of the protein into which a gene is translated, and developing reaction catalysts.

DESCRIPTION OF THE PREFERRED EMBODIMENTS (Functional Molecule and Process for Producing the Same)

A functional molecule according to the present invention is produced by the process for producing the functional molecule according to the present invention. Below, details of the functional molecule according to the present invention will be described with an explanation of the process for producing the functional molecule according to the present invention.

The process for producing the functional molecule according to the present invention includes at least a forming step and a producing step, preferably includes a selecting step, a determining step, and a translating step, and additionally includes other steps properly selected in accordance with a purpose.

Forming Step

The forming step is a step of forming a modified nucleotide n-mer (where, n represents an integer) containing a modified nucleoside prepared by introducing a substituent into a nucleoside composing a nucleic acid.

The modified nucleotide n-mer comprises the modified nucleotide.

The modified nucleotide is prepared by introducing a substituent into a nucleoside constructing the nucleic acid.

n in the modified nucleotide n-mer represents an integer, is preferably 2 or more, more preferably 2 to 10, particularly preferably 2 to 3.

When the n is less than 2, number of kinds of the modified nucleotide is not almost different from 4 kinds of nucleotide composing the nucleic acid to cause sometimes impossible improvement of an ability of recognizing the target. When the n is 4 or more, 1 base lack or 1 base addition, which may be caused during the amplification step, can be difficultly distinguished from others due to base sequence similarity and, when n is 3, different side chains of 64 kinds in a maximum can be introduced. Therefore, in consideration of that various kinds of proteins are made up from 20 kinds of amino acids, 3 is satisfactory for n and, thus, n of 4 or more numbers provides insufficient effect as the result of forming step and, on the contrary, a fear arises in an increase in a load on the synthesis.

The nucleic acid includes either DNA or RNA, and the DNA or RNA may have a single-strand structure or a double-strand structure.

The DNA has 4 bases, which are adenine (A), thymine (T), guanine (G) and cytosine (C), the bases in a DNA polynucleotide chain are present in a form projecting to an inside each other in a plane vertical to a central axis to make the so-called Watson-Click model base pair and thymine and cytosine make specifically hydrogen bonds to adenine and guanine, respectively. As the result, in the double-stranded DNA, 2 polynucleotide chains are complementarily bonded to each other.

The 4 kinds of nucleosides (deoxyribonucleosides) of the DNA include deoxyadenosine (dA), deoxyguanosine (dG), deoxycytidine (dC) and thymidine (T).

The RNA has 4 bases, which are adenine (A), guanine (G), uracil (U) and cytosine (C), and classified into 3 kinds, which are ribosome RNA (rRNA), transfer RNA (tRNA) and messenger RNA (mRNA).

The 4 kinds of nucleosides (ribonucleosides) of the RNA include adenosine (A), guanosine (G), cytidine (C) and uridine (U).

A modified nucleotide dimer in the case where n is 2 in the modified nucleotide n-mer is not restricted, and can be selected properly in accordance with the purpose. For example, it may be a combination of 4 kinds of nucleosides constructing the nucleic acid with the modified nucleoside, or may be a combination of the modified nucleosides. In this connection, the substituent may not be introduced into the nucleoside (a saccharide is bonded to a purine or pyrimidine base), but may be into nucleotide (a phosphate group is added to the nucleoside).

A position in the modified nucleoside, into which the substituent may be introduced in the modified nucleoside, is not specially restricted, and can be selected properly in accordance with the purpose, including, for example, the 5th position in pyrimidine, the 7th position in purine, the 8th position in purine, substitution of an amine outside a ring, substitution of 4-thiouridine, substitution of 5-bromo, substitution of 5-iodide uracil, and the like. Among these substitutions, in consideration of scarcely inhibiting an enzyme reaction at amplification (replication), the 5th position in pyrimidine and the 7th position in purine are preferable and the 5th position in pyrimidine is more preferable because of easy synthesis.

A process for introducing a substituent into the nucleoside is not specially restricted, and can be selected properly in accordance with the purpose, including, for example, preferably the process shown in the following formula, in which substituent R is introduced into the 5th position in pyrimidine base of the nucleoside.

The substituent R is not specially restricted, and can be selected properly in accordance with the purpose, including, for example, natural or nonnatural amino acids, metal complexes, fluorescent dyes, oxidation-reduction pigments, spin label compounds, hydrogen atom, alkyl groups having carbon number ranging from 1 to 10, and groups represented by the following formulae (1) to (10).

(1)
(2)
(3)
(4)
(5)
(6)
(7)

-continued (8)

(9)

(10)

The natural or nonnatural amino acids are not specially restricted, and can be selected properly in accordance with the purpose, including, for example, valine, leucine, isoleucine, alanine, arginine, glutamine, lysine, aspartic acid, glutamic acid, proline, cysteine, threonine, methionine, histidine, phenylalanine, tyrosine, tryptophane, asparagine, glycine, serine, and the like.

The metal complex is not specially restricted, and can be selected properly in accordance with the purpose as long as it is a compound in which a ligand is coordinated with a metal ion, including, for example, Ru-bipyridil complex, ferrocene complex, nickel imidazole complex, and the like.

The fluorescent dyes are not specially restricted, and can be selected properly in accordance with the purpose, including, for example, fluorescent dyes such as fluorescein dyes, rhodamine dyes, eosine dyes, NBD dyes, and the like.

The oxidation-reduction pigments are not specially restricted, but can be selected properly in accordance with the purpose, including, for example, leuco pigments such as leucoaniline, leucoanthocyanine, and the like.

The spin label compounds are not specially restricted, and can be selected properly in accordance with the purpose, including, for example, iron N-(dithiocarboxy) sarcosine, TEMPO (tetramethyl piperidine) derivatives, and the like.

The alkyl groups having carbon number ranging from 1 to 10 are not specially restricted, and can be selected properly in accordance with the purpose, including, for example, a methyl group, ethyl group, propyl group, isopropyl group, butyl group, isobutyl group, tert-butyl group, pentyl group, neopentyl group, hexyl group, cyclohexyl group, octyl group, nonyl group, decyl group and the like.

These may be further substituted by a substituent.

The process for synthesizing the modified nucleotide dimer is not specially restricted, and can be selected properly in accordance with the purpose, including, for example, a diester method, triester method, phosphite method, phosphoroamidite method, H-phosphonate method, thiophosphite method, and the like. Among these methods, the phosphoroamidite method is preferable.

The phosphoroamidite method is, as a rule, employs a condensation reaction of nucleoside phosphoroamidite to the nucleoside as a key reaction using tetrazole as an enhancer. This reaction usually occurs competitively in both a hydroxyl group of a saccharide part and an amino group of a base part of the nucleoside. However, in order to realize the desired nucleotide synthesis, the reaction should occur selectively only in the hydroxyl group of the saccharide part. Hence, for inhibition of a side reaction to the amino group, modification reaction is required using a protecting group. For example, the modified nucleotide dimer ($AU_1$) can be, as shown by the following formula, synthesized from deoxyadenosine and modified deoxyuridine.

phosphoamidite (AU₁)

Where, in the formula, DMTr represents a dimethoxy trityl group.

The modified nucleotide dimers ($AC_1$, $C_2A$, $C_3C$, $C_4G$, $C_5T$, $GC_6$, $GU_2$, $U_3A$, $U_4C$, $U_5G$, and $U_6T$), which are represented in the relation table of the following Table 1 mentioned later, can be also synthesized by the similar method.

Where, the synthesized modified nucleotide dimer is made in a one-to-one combination (relation) with any one of 16 nucleosides in the relation table, which is made by combining 4 kinds of nucleosides constituting the nucleic acid, in a one-to-one format.

When kinds of the modified nucleotide dimer is less than 5, there is no large difference from 4 kinds of nucleotides constituting the nucleic acid to invite insufficient improvement of the ability of recognizing the target.

The relation table is, for example, exemplified by that shown in the following Table 1. In this Table 1, bases of 4 kinds of nucleosides are transversely (5' direction) arranged in the order of A, C, G and T and, on the other hand, bases of 4 kinds of nucleosides are longitudinally (3' direction) arranged in the order of A, C, G and T, and 16 patterns (boxes) are formed by relating these bases to each other one-to-one.

Similarly to the case of the modified nucleotide dimer, a modified nucleotide trimer can be used. The relation table in this case, for example, includes that shown in the following Table 2. In Table 2, 56 patterns (56 kinds of modified nucleotide trimer) are formed. Similarly to the case of the modified nucleotide dimer and the modified nucleotide trimer, a modified nucleotide n-mer (n representing the integer) can be used. In the relation table in this case, $4^n$ patterns ($4^n$ kinds of the modified nucleotide n-mer) can be made.

TABLE 1 relation table

| 3' \ 5' | A | C | G | T |
|---|---|---|---|---|
| A |  | $C_2A$ |  | $U_3A$ |
| C | $AC_1$ | $C_3C$ | $GC_6$ | $U_4C$ |
| G |  | $C_4G$ |  | $U_5G$ |
| T | $AU_1$ | $C_5T$ | $GU_2$ | $U_6T$ |

TABLE 2

|  |  | A | | C | | G | | T | |
|---|---|---|---|---|---|---|---|---|---|
| A | A | / | / | A $C_2AA$ | G $C_3AG$ | / | / | A $U_3AA$ | G $U_4AG$ |
|  | C | C $AAC_1$ | T $AAU_1$ | C $C_4AC$ | T $C_5AT$ | C $GAC_6$ | T $GAU_2$ | C $U_5AC$ | T $U_6AT$ |
| C | A | A $AC_7A$ | G $AC_8G$ | A $C_{11}CA$ | G $C_{12}CG$ | A $CG_{15}A$ | G $GC_{16}G$ | A $U_7CA$ | G $U_8CG$ |
|  | C | C $AC_9C$ | T $AC_{10}T$ | C $C_{13}CC$ | T $C_{14}CG$ | C $CG_{17}C$ | T $GC_{18}T$ | C $U_9CC$ | T $U_{10}CT$ |
| G | A | / | / | A $C_{20}GA$ | G $C_{21}GG$ | / | / | A $U_{13}GA$ | G $U_{14}GG$ |
|  | C | C $AGC_{19}$ | T $AGU_{11}$ | C $C_{22}GA$ | T $C_{23}GT$ | C $GGC_{24}$ | T $GGU_{12}$ | C $U_{15}GC$ | T $U_{16}GT$ |
| T | A | A $AU_{17}A$ | G $AU_{18}G$ | A $C_{25}TA$ | G $C_{26}TG$ | A $GU_{21}A$ | G $GU_{22}T$ | A $U_{25}TA$ | G $U_{26}TG$ |
|  | C | C $AU_{19}C$ | T $AU_{20}T$ | C $C_{27}TC$ | T $C_{28}TT$ | C $GU_{23}C$ | T $GU_{24}T$ | C $U_{27}TC$ | T $U_{28}TT$ |

In the relation table in Table 1, as shown below, 12 kinds of the modified nucleotide dimer are conditioned.

Specifically, a base sequence is read from a 5' side to a 3' side directions and a base sequence AC corresponds to the modified nucleotide dimer $AC_1$. A sequence AT corresponds to the modified nucleotide dimer $AU_1$. A base sequence CA corresponds to the modified nucleotide dimer $C_2A$. A base sequence CC corresponds to the modified nucleotide dimer $C_3C$. A base sequence CG corresponds to the modified nucleotide dimer $C_4G$. A base sequence CT corresponds to the modified nucleotide dimer $C_5T$. A base sequence GC corresponds to the modified nucleotide dimer $GC_6$. A base sequence GT corresponds to the modified nucleotide dimer $GU_2$. A base sequence TA corresponds to the modified nucleotide dimer $U_3A$. A base sequence TC corresponds to the modified nucleotide dimer $U_4C$. A base sequence TG corresponds to the modified nucleotide dimer $U_5G$. A base sequence TT corresponds to the modified nucleotide dimer $U_6T$.

Conditioning of a base sequence and the modified nucleotide dimer in the relation table in Table 1 is not specially restricted, but can be selected properly in accordance with the purpose. Table 1 is simply an example. When it is difficult to prepare 12 kinds of the modified nucleotide dimer, a portion may be duplicated. However, it may result in lowering the recognition ability to the target.

For AA, AG, GA and GG being combinations of purine bases in the relation table in Table 1, no modified nucleotide dimer was prepared due to a lower reactivity of an enzyme used for modifying the purine base. This does not mean that the modified nucleotide dimer containing the purine bases cannot be prepared.

On the basis of the relation table in Table 1, making a relation between 12 kinds of dimer modified-nucleosides allows increasing the 4 kinds in the conventional nucleic acid to 12 kinds to enable to express distinguishing ability to many kinds of the target.

Producing Step

The producing step is a step of producing a modified oligonucleotide sequence by randomly polymerizing a modified nucleotide n-mer (n representing an integer) containing a modified nucleoside prepared by inserting a substituent into the nucleoside composing the nucleic acid.

A reaction product, which contains the modified oligonucleotide sequence obtained as a result of carrying out the producing step, can be used in the selecting step and the like as a random polymer pool containing the modified oligonucleotide sequence, intactly without separation and purification steps.

Figure 1:
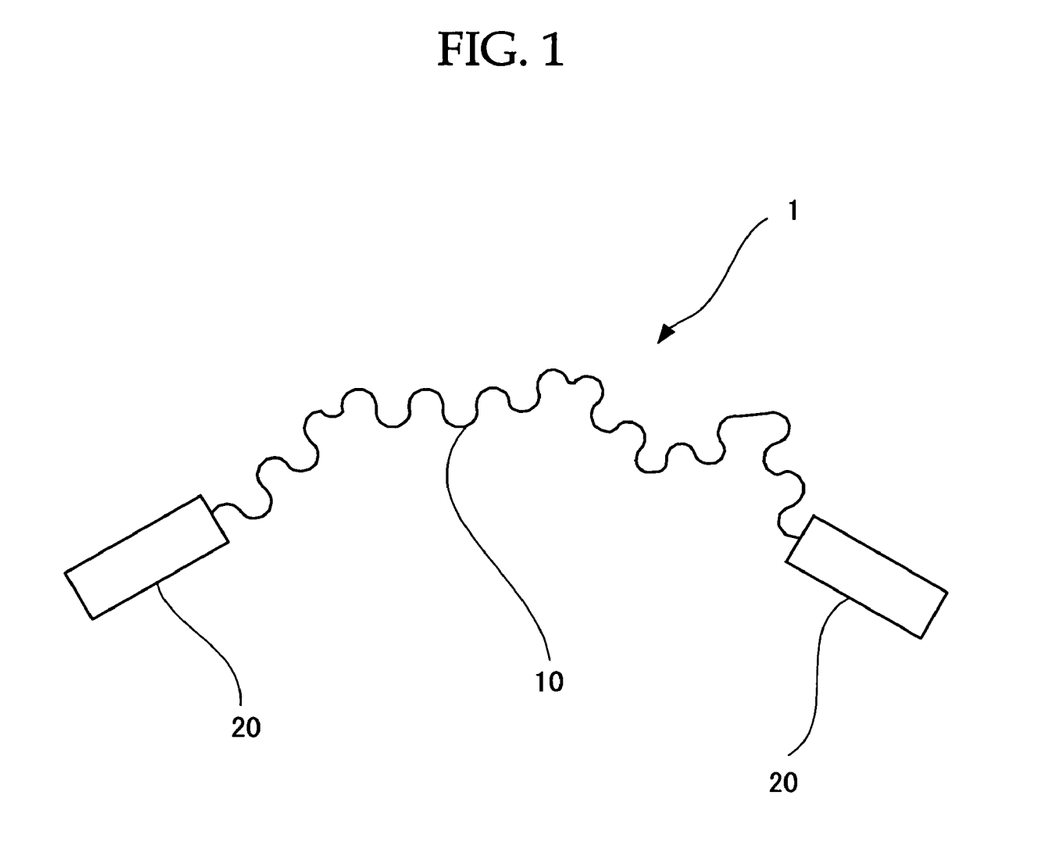
FIG. 1 is a diagrammatic view showing an example of an oligonucleotide composed of a modified oligonucleotide and a fixed oligonucleotide, which compose a random polymer pool.

For oligonucleotide 1 composing the random polymer pool, as shown in FIG. 1, it is preferable that both ends of the modified oligonucleotide sequence 10 have the fixed oligonucleotide sequence 20 and 20 in consideration of efficient amplification (replication) by attaching a primer to the fixed oligonucleotide sequence portion at PCR operation in the determining step mentioned later.

The number of nucleotide of the modified oligonucleotide sequence is not specially restricted, and can be selected properly in accordance with the purpose; 10 to 100 nucleotides are preferable and 10 to 50 nucleotides are more preferable.

The number of nucleotide of the fixed oligonucleotide sequence is not specially restricted, and can be selected properly in accordance with the purpose; usually 15 or more nucleotides are preferable and 20 to 40 nucleotides are more preferable.

The process for preparing the random polymer pool is not specially restricted, and can be selected from publicly known methods properly in accordance with the purpose; for example, a method using a DNA synthesizer (automated DNA synthesizer) is preferable.

Figure 2:
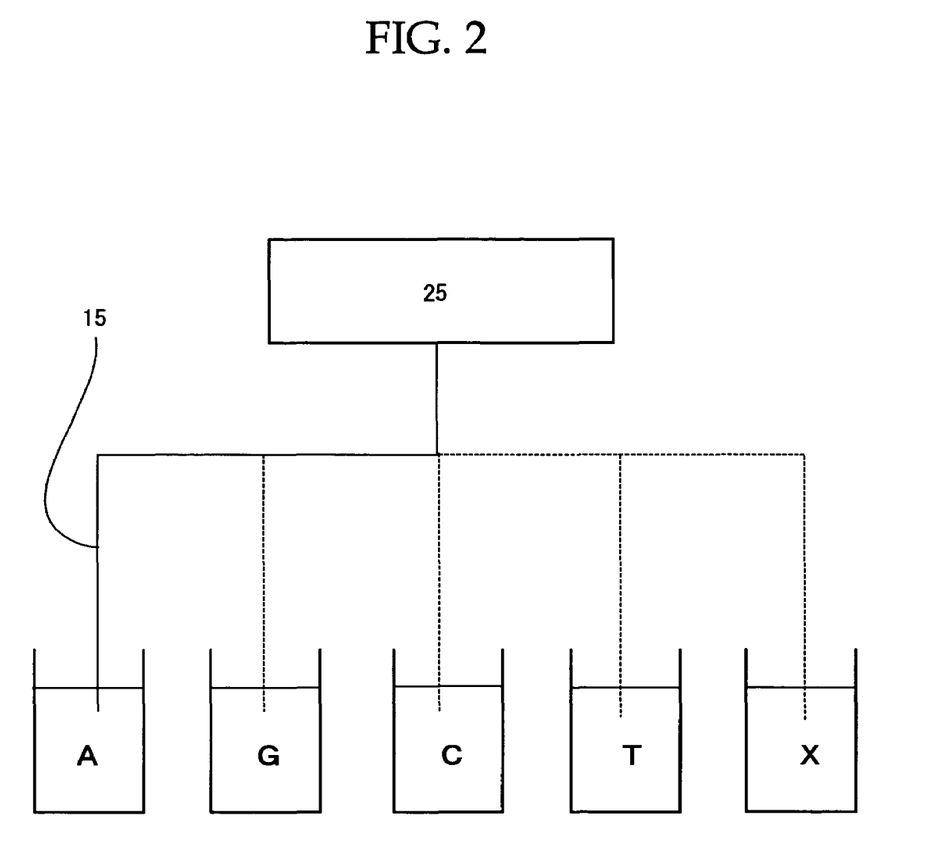
FIG. 2 is a schematic view showing an example of a DNA synthesizer used for synthesizing the random polymer pool.

The method using the DNA synthesizer (automated DNA synthesizer) is not specially restricted, but can be selected properly in accordance with the purpose; preferable process is that by using the DNA synthesizer (automated DNA synthesizer) as shown in FIG. 2, using a mixture (there are 12 kinds in the example shown in FIG. 2; expressed as "X" in FIG. 2) of a plurality of kinds of the synthesized modified nucleotide dimer as a reagent, sucking this reagent up by nozzle 15 to polymerize under control of a controller 25, and then, finally preparing the random polymer pool having the modified oligonucleotide sequence with all sequence orders randomly arranged. This case is advantageous in the point that the random polymer pool is efficiently prepared.

For synthesizing the fixed nucleotide sequence, similar method can be used by using 4 kinds, i.e., adenine (A), thymine (T), guanine (G) and cytosine (C.)

The process for preparing the random polymer pool also includes a process in which monomer blocks are aligned to the previously prepared oligonucleotide random sequence to carry out annealing and a DNA ligase or an RNA ligase are worked to ligate them for preparation of the random polymer pool. Also in this case, the process can prepare the random polymer pool containing the modified oligonucleotide sequence having all sequence orders randomly arranged.

The DNA ligase is an enzyme to catalyze formation of a covalent bond between the 5' phosphate group and the 3' hydroxyl group of adjacent nucleotides.

The RNA ligase is the enzyme to ligate a polynucleotide of the terminal of 5' phosphate group and the polynucleotide of the terminal of 3' hydroxyl group. A substrate of the RNA ligase is normally RNA, however, a polydeoxyribonucleotide of the terminal of 5' phosphate group and the polydeoxyribonucleotide of which 3' terminal only is ribonucleotide ligate efficiently.

The random polymer pool contains the modified oligonucleotide sequence and, if required, may further contain a sequence which is prepared by polymerizing randomly monomers or oligomers of the DNA or RNA not modified by a substituent.

Selecting Step

The selecting step is a step of selecting one having an affinity with the target from the modified oligonucleotide sequence.

The selection method is not specially restricted, and can be selected from publicly known methods properly in accordance with the purpose, including, for example, various methods such as affinity chromatography, filter binding assay, liquid-liquid partition, filtration, gel shift, density gradient centrifugation. These methods may be conducted in 1 method independently and may be conducted in 2 or more methods. Among these methods, affinity chromatography is preferable.

The affinity chromatography is a separation and purification means by applying the biological affinity by which specific components are easy to bind each other. Specifically, the target is immobilized in a column filler such as a resin to be equilibrated with a buffer solution for attachment, and then, a solution containing the random polymer pool is poured into a column to leave stand under a certain condition. The oligonucleotide sequence having affinity with the target adsorbs to the column, and sufficient washing with the buffer solution for attachment allows removing left components other than the oligonucleotide sequence. Passing the solution containing the target or a diluted buffer solution through the column enables to collect and select oligonucleotide containing the modified oligonucleotide sequence.

In the case where the target is unknown and present in a large kinds (for example, organs and blood serum), means of the selection is preferably a method in which 2 or more targets are immobilized on a matrix having a linear to cubic spatial arrangement, the random polymer pool containing the modified oligonucleotide sequence is worked on the matrix on which the target has been immobilized, and then, the modified oligonucleotide sequence attached to the target is purified.

The process for immobilizing the target on the matrix is not specially restricted, and can be selected in accordance with the purpose. For example, when the target is a protein, a western blotting method in which the target is subjected to polyacrylamide electrophoresis (for example, SDS-PAGE and the like) and, then, transferred to the membranous matrix, a dot blotting method and slot blotting method in which the target or diluted solution thereof is directly impregnated into the membranous matrix, and the like. Among these methods, the western blotting method is preferable in consideration of that a trace amount of the protein contained in the solution of a complicated composition such as a cell extract can be clearly detected.

The western blotting method is an approach for detecting a specific protein from a protein mixture by using combination of an excellent separation performance of electrophoresis with high specificities of an antigen-antibody reaction, and also is the method in which SDS-PAGE, isoelectric focusing, or 2-dimensional electrophoresis is conducted and, then, the protein is electrically moved from a gel to and immobilized on the membranous matrix. The membranous matrix is not specially restricted, and can be selected in accordance with the purpose, including, for example, highly hydrophobic nitrocellulose film, to which the protein is easy to be bound, and excellently hydrophobic PVDF (polyvinylidene difluoride) film.

In the present invention, the target is preferably labeled, for example, with at least one of labeling materials selected from radioisotopes, chemiluminescence materials, fluorescent materials, enzymes, antibodies, ligands and receptors; or the modified oligonucleotide sequence contained in the random polymer pool is preferably labeled with at least one of labeling materials selected from radioisotopes, chemiluminescence materials, fluorescent materials, enzymes, antibodies, ligands and receptors.

The radioisotope includes, for example, $^{32}P$, $^{33}P$ $^{35}S$ and the like.

The chemiluminescence material includes, for example, acridinium ester, luminol, isoluminol, or these derivatives, and the like. Detection by using the chemiluminescence requires exposure detection to an X-ray film or a scanner capable of detecting chemiluminescence, however, has an advantage of easy detection of a trace protein due to a higher sensitivity than other coloration methods by 10 to 50 folds or more.

The fluorescent material includes, for example, fluorescent dyes such as fluorescein series, fluorescein series, rhodamine series, eosine series and NDB series, green fluorescent protein (GFP), chelates of rare earths such as europium (Eu), terbium (Tb) and samarium (Sm), tetramethyl rhodamine, Texas Red, 4-methyl umbelliferone, 7-amino-4-methyl coumarin, Cy3, Cy5, and the like.

The enzyme includes, for example, peroxidase, alkaline phosphatase, glucose oxidase, beta-galactosidase, luciferase, and the like.

In addition, the labeling materials include biotin, ligand, a specific nucleic acid, protein, hapten, and the like. Possible combinations are that when the labeling material is biotin, avidin or streptavidin specifically binding to this, that when the labeling material is hapten, an antibody specifically binding to this, that when the labeling material is a ligand, the receptor, and that when the labeling material is the specific nucleic acid, protein, hapten and the like, the specific nucleic acid, a nucleic acid-binding protein, a protein having the affinity to the specific protein, respectively.

The process for purification is not specially restricted, but can be selected in accordance with the purpose. For example, a particularly preferable method is that the modified oligonucleotide sequence, which has been immobilized on a predetermined position (domain) on the membranous matrix (a membrane such as a nitrocellulose film) by the western blotting method and attached to the target, is cut at every predetermined position (domain) together with the matrix (the membrane such as a nitrocellulose film) to yield a fragment and, then, the modified oligonucleotide sequence is collected from the cut piece. This way is advantageous in the point that no special purification step is required and the modified oligonucleotide sequence can be efficiently and conveniently purified. Also, it is advantageous in the point that the modified oligonucleotide sequences different between the predetermined positions (domains) can be efficiently purified.

Collecting the modified oligonucleotide sequence from the cut piece can be carried out by applying a voltage using an ionic solution by electroelution or by using a hot water.

The purification may be carried out by another method, in which the modified oligonucleotide is dissociated from the target, monitoring a dissociation constant of the target and the modified oligonucleotide sequence. In this case, the functional molecule having the desired dissociation constant can be selected through a minimal 1 processing. Thus, measuring the dissociation constant and controlling the dissociation constant in the selecting step enables to select the functional molecule efficiently. The dissociation constant can be properly set in accordance with the target. For example, it can be measured by using a measuring instrument using surface plasmon resonance.

According to the present invention, in the selecting step, by using an interaction between 2 or more kinds of molecules having different dissociation constants, for example, the functional molecule is selected by a washing operation matching a smaller dissociation constant and, on the other hand, by a drastic washing operation matching a larger dissociation constant, a carrier for selection can be regenerated. In this method, even when the targets are 2 or more, regeneration becomes possible and, therefore, a plurality of the functional molecule can be efficiently selected in a unit by using a single substrate to eliminate waste losses and reduce a cost.

On the other hand, in the selecting step, one-to-one relation of linkers having different reactivities to a plurality of molecules allows selecting orderly the functional molecules capable of recognizing individual molecules by different posttreatments. By these steps, the functional molecules can be selected. In this way, using commonly the random polymer pool enables efficient selection of a plurality of the functional molecules.

The different posttreatments include a process for flowing a reagent capable of adjusting a binding strength of the linker, a process for flowing a reagent capable of adjusting a cleaving easiness of the linker bond, and a process using a reaction to cut selectively a specific position by an optical reaction or electrode reaction.

The target (target material) is not specially restricted, and can be selected properly in accordance with the purpose, including, for example, proteins, lipoproteins, sugar proteins, polypeptides, lipids, polysaccharides, lipopolysaccharides, nucleic acids, environmental hormones, drugs, a complex of these substances, and the like. These substances can be used independently and may be used in combination of 2 or more kinds. Among these substances, preferable ones are plasma protein, tumor marker, apoprotein, virus, autoantibody, coagulation and fibrinolysis factor, hormone, drug in blood, HLA antigen, environmental hormone, nucleic acid, and the like.

The plasma protein includes, for example, immunoglobulin (IgG, IgA, IgM, IgD, IgE), component of complement (C3, C4, C5, C1q), CRP, $\alpha_1$-antitrypsin, $\alpha_1$-microglobulin, $\beta_2$-microglobulin, haptoglobin, transferrin, ceruloplasmin, ferritin, and the like.

The tumor marker includes, for example, α-fetoprotein (AFP), carcinoembryonic antigen (CEA), CA19-9, CA125, CA15-3, SCC antigen, prostatic acid phosphatase (PAP), PIVKA-II, γ-seminoprotein, TPA, elastase I, nerve specific enolase (NSE), immunosuppressive acid protein (IAP), and the like.

The apoprotein includes, for example, apoA-I, apoA-II, apoB, apoC-II, apoC-III, apoE, and the like.

The virus includes, for example, hepatitis type B virus (HBV), hepatitis type C virus (HCV), HTLV-I, HIV, and the like. In addition, infectious diseases caused by pathogens other than virus include ASO, *toxoplasma, mycoplasma*, STD, and the like.

The autoantibody includes, for example, antimicrosome antibody, anti-thyroglobulin antibody, antinuclear antibody, rheumatism factor, antimitochondrial antibody, myelin antibody, and the like.

The coagulation and fibrinolysis factor includes, for example, fibrinogen, fibrin decomposition product (FDP), plasminogen, $\alpha_2$-plasmin inhibitor, antithrombin III, β-thromboglobulin, factor VIII, protein C, protein S, and the like.

The hormone includes, for example, pituitary hormones (LH, FSH, GH, ACTH, TSH, prolactin), thyroid hormones ($T_3$, $T_4$, thyroglobulin), calcitonin, parathyroid hormone (PTH), adrenocortical hormones (aldosterone, cortisol), gonad hormones (hCG, estrogen, testosteron, hPL), pancreas digestive tract hormones (insulin, C-peptide, glucagon, gastrin), others (renin, angiotensin I, II, encephalin, erythropoietin), and the like.

The environmental hormone is a exogenous endocrine disrupting chemicals widely distributed in the ambient world and taken in organisms in accordance with daily activities to influence to various physiological endocrine phenomena such as reproduction, ontogenesis, and behaviors. The environmental hormone includes, for example, nonyl phenol, octyl phenol, bisphenol A, butyl benzyl phthalate, tributyltin, PCB, polychlorinated dibenzodioxin, polychlorinated dibenzofuran, dioxins, DDT, DDE, DDD, endosulfan, methoxychlor, heptachlor, toxaphen, dieldrin, lindane, diethylstilbestrol (DES), ethynyl estradiol (component of the Pill), coumestrol, formononetein, Genistein, and the like.

The drug in blood includes, for example, antiepileptic agents such as carbamazepin, primidon and valproic acid, circulatory disease drugs such as digoxin, chinidine, digitoxin and theophylline, and antibiotics such as gentamycin, kanamycin and streptomycin, and the like.

The nucleic acid includes, for example, gene related to cancer, gene related to genetic disease, virus gene, bacterial gene and gene showing polymorphism called a risk factor of a disease, and the like.

The gene related to cancer includes, for example, k-ras gene, N-ras gene, p53 gene, BRCA1 gene, BRCA 2 gene, src gene, and ros gene or APC gene, and the like.

The gene related to genetic disease includes, for example, those related to various inborn errors of metabolism such as phenylketonuria, alcaptonuria, cystinuria, Huntington's chorea, Down's syndrome, Duchenne muscular dystrophy, angiostaxis, and the like.

The virus and bacterial genes include, for example, hepatitis C virus, hepatitis B virus, influenza virus, measles virus, HIV, *mycoplasma, Rickettsia, streptococcus, Salmonella*, and the like.

The gene showing polymorphism includes, for example, gene having the base sequence, which is not necessarily related to directly a cause of a disease and is different between individuals, such as PS1 (preselinin 1) gene, PS2 (preselinin 2) gene, APP (β-amyloid precursor protein) gene, lipoprotein gene, gene related to HLA (Human Leukocyte Antigen) or blood group, or gene related to onset of hypertension and diabetes.

A sample containing the target includes, for example, pathogens such as bacteria and virus, blood, saliva and an affected tissue piece collected from organisms, or excretes such as feces and urine. In addition, when prenatal diagnosis is conducted, it may include a fetal cell presenting in amniotic fluid, a portion of dividing egg cells in vitro, and the like. These samples may be previously subjected to a cytocidal treatment such as an oxygen treatment, heat treatment, surfactant treatment, ultrasonication treatment or a combination of these operations directly or, if required, after being subjected to condensation by centrifugal operation or the like as sedimentation.

Determining Step

The determining step is a step for amplifying the modified oligonucleotide sequence, which has been selected by the selecting step, to determine the base sequence.

The amplification method is not specially restricted as long as it can amplify the number of the targeted modified oligonucleotide sequence, and can be selected properly from methods publicly known in the technical field, including, for example, the PCR (Polymerase Chain Reaction) method, LCR (Ligase Chain Reaction) method, 3SR (Self-sustained Sequence Replication) method, SDA (Strand Displacement Amplification) method, RT-PCR method, ICAN method, LAMP method, and the like. These methods may be conducted in 1 method independently or in 2 or more methods.

The PCR method means Polymerase Chain Reaction method and the method can amplify the specific oligonucleotide region some by hundred thousand folds by repeating the DNA synthesis reaction in vitro by DNA synthetase. According to the PCR method, the primer elongation reaction is carried out by taking-in of 4 kinds or 5 kinds of nucleotide triphosphate (deoxyadenosine triphosphate, deoxyguanosine triphosphate, deoxycytidine triphosphate, and deoxythymidine triphosphate or deoxyuridine triphosphate (a mixture of these compounds may be also called dNTP) as a substrate into the primer.

For carrying out this elongation reaction, an amplification reaction reagent containing the unit nucleic acid and a nucleic acid elongation enzyme is usually used for amplifying a nucleic acid chain.

In this case, the usable nucleic acid elongation enzymes include arbitrary DNA polymerases such as *E. coli* DNA polymerase I, Klenow fragment of *E. coli* DNA polymerase I, T4 DNA polymerase and the like. Particularly, heat-stable DNA polymerases such as Taq DNA polymerase, Tth DNA polymerase, Vent DNA polymerase and the like can be preferably used. By using these enzymes, there is no necessity of adding a new enzyme for every cycle to enable to repeat the cycle automatically, set an annealing temperature to 50° C. to 60° C., and thus the specificity of target base sequence recognition by the primer can be increased and the gene amplification reaction can be quickly and specifically carried out (Japanese Patent Application Laid-Open (JP-A) No. 01-314965 and 01-252300).

At carrying out this reaction, an oil can be added to prevent evaporation of water contained in a reaction solution. In this case, the oil is sufficient to be that possible to make a distribution between the oil and water and has a smaller specific gravity than that of water. Specifically, silicone oil, mineral oil and the like are exemplified. Further, according to a gene amplification instrument, such the medium is not needed, and the primer elongation reaction can be also conducted by using such the gene amplification instrument.

As described above, repeating the elongation reaction by using the primer enables to operate efficient gene amplification of the target oligonucleotide to yield a large amount of the oligonucleotide. The specific method including conditions for the gene amplification reaction includes the publicly known methods described in references such as Zikken Igaku (Yodosha, 8, No. 9. 1990), PCR Technology (Stockton Press, 1989), and the like.

According to conducting the PCR method, the modified oligonucleotide sequence is substituted for a natural oligonucleotide sequence having no modified substituent.

When the modified oligonucleotide sequence is not the DNA but the RNA, the DNA can be synthesized by performing a reverse transcription reaction. The reverse transcription reaction is a process for synthesizing the DNA by using the RNA as a template. A reaction solution and a reaction condition of the reverse transcription reaction are different in accordance with a target RNA. For instance, operations comprise adding an RNase-free sterilized distilled water and a 3'-primer to an RNA solution and incubating and, then, cooling and adding a reverse transcription buffer solution, which includes Tris-HCl, KCl, $MgCl_2$ and the like, DTT, and dNTPs, and adding a reverse transcriptase followed by incubation. Stopping the reverse transcription reaction can be operated by adjusting conditions of the incubation. Such the reverse transcription reaction can be also performed by a reverse transcription PCR.

The process for determining the base sequence of the amplified oligonucleotide is not specially restricted, and can be selected properly from methods publicly known in the technical field in accordance with the purpose, including, for example, a method by gene cloning, chain terminator method, Sanger method, a DNA sequencer (automated DNA base sequence determination equipment) by using a dideoxy method, and the like. These methods may be employed in 1 method independently or in 2 or more methods.

By the gene cloning, produce can be operated by transforming a host cell by an expression vector, into which the amplified oligonucleotide sequence is incorporated, followed by culturing this transformant.

The expression vector includes, for example, a plasmid vector, a phage vector, a chimera vector prepared from a plasmid and a phage, and the like.

The host cell includes, for example, prokaryotes such as *Escherichia coli* and *Bacillus subtilis*, eukaryotes such as yeast, an animal cell, and the like.

Translating Step

The translating step is a step of translating the sequence of the modified oligonucleotide sequence, of which base sequence has been determined, on the basis of the relation table prepared by relating at least one of $4^n$ nucleotide n-mers, which are presented in the relation table prepared by the one-to-one combination of 4 nucleosides, to a modified nucleotide n-mer.

The translating step translates the base sequence of the oligonucleotide amplified by the determining step to determine the base sequence on the basis of the relation table prepared by relating at least one of $4^n$ nucleotide n-mers (n representing an integer), which are presented in the relation table prepared by the one-to-one combination of 4 nucleosides, to a modified nucleotide n-mer (n representing the integer).

The translation is preferably carried out for every n base from the 5' terminal side of the modified oligonucleotide sequence made of the modified nucleotide n-mer, of which base sequence has been determined, on the basis of the relation table. It is more preferable to insert a fixed base to define a block periodically. For instance, when the modified nucleotide n-mer is a modified nucleotide dimer, the translation is carried out for every 2 base from the 5' terminal side of the modified oligonucleotide sequence, of which base sequence has been determined, made of the modified nucleotide dimer on the basis of the relation table. Practically, the translation is carried out on the basis of the relation table expressed by the following Table 1.

TABLE 1

| | relation table | | | |
|---|---|---|---|---|
| | | 5' | | |
| 3' | A | C | G | T |
| A | | $C_2A$ | | $U_3A$ |
| C | $AC_1$ | $C_3C$ | $GC_6$ | $U_4C$ |
| G | | $C_4G$ | | $U_5G$ |
| T | $AU_1$ | $C_5T$ | $GU_2$ | $U_6T$ |

Figure 3A:
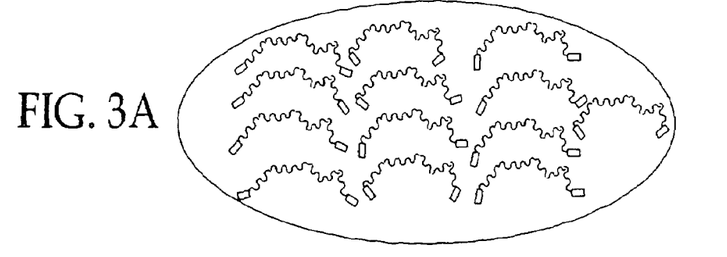
FIG. 3A is a schematic view explaining a status, where the random polymer pool was synthesized, in a process for producing a functional molecule according to the present invention.
Figure 3B:
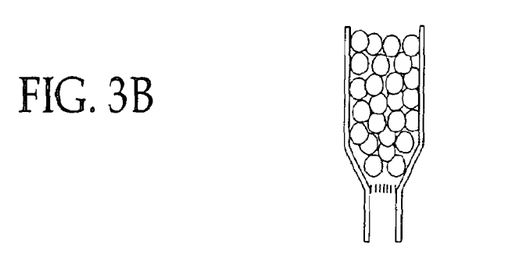
FIG. 3B is a schematic view showing an example of an affinity column.
Figure 3C:
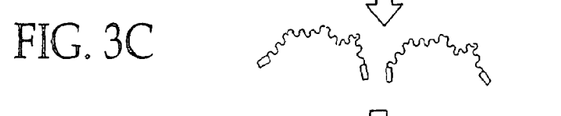
FIG. 3C is a schematic view explaining a state, where an oligonucleotide containing a random sequence of a modified nucleotide is selected and collected.
Figure 3D:
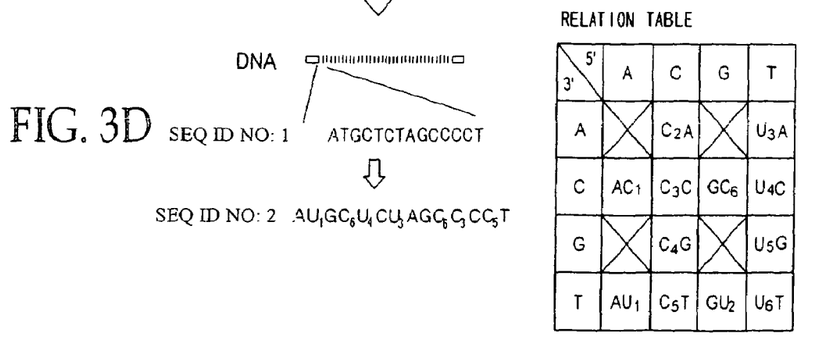
FIG. 3D is a schematic view explaining a state, where the modified oligonucleotide sequence selected was amplified by PCR, and the sequence thereof is determined and translated.

For instance, as shown in FIG. 3D, when the determined modified oligonucleotide sequence is "ATGCTCTAGC-CCCT," (SEQ ID NO: 1), it is confirmed that the sequence is translated into "$AU_1GC_6U_4CU_3AGC_6C_3CC_5T$" (SEQ ID NO: 2), on the basis of the relation table, to thereby know the sequence of the functional molecule.

When the modified nucleotide n-mer is a modified nucleotide trimer, the translation is carried out for every 3 base from the 5' terminal side of the modified oligonucleotide sequence, of which base sequence has been determined, made of the modified nucleotide trimer on the basis of the relation table. Practically, the translation is carried out on the basis of the relation table expressed by the following Table 2.

TABLE 2

|   | A | | C | | G | | T | |
|---|---|---|---|---|---|---|---|---|
| A | A | G | A<br>$C_2AA$ | G<br>$C_3AG$ | A | G | A<br>$U_3AA$ | G<br>$U_4AG$ |
|   | C<br>$AAC_1$ | T<br>$AAU_1$ | C<br>$C_4AC$ | T<br>$C_5AT$ | C<br>$GAC_6$ | T<br>$GAU_2$ | C<br>$U_5AC$ | T<br>$U_6AT$ |
| C | A<br>$AC_7A$ | G<br>$AC_8G$ | A<br>$C_{11}CA$ | G<br>$C_{12}CG$ | A<br>$GC_{15}A$ | G<br>$GC_{16}G$ | A<br>$U_7CA$ | G<br>$U_8CG$ |
|   | C<br>$AC_9C$ | T<br>$AC_{10}T$ | C<br>$C_{13}CC$ | T<br>$C_{14}CT$ | C<br>$GC_{17}C$ | T<br>$GC_{18}T$ | C<br>$U_9CC$ | T<br>$U_{10}CT$ |
| G | A | G | A<br>$C_{20}GA$ | G<br>$C_{21}GG$ | A | G | A<br>$U_{13}GA$ | G<br>$U_{14}GG$ |
|   | C<br>$AGC_{19}$ | T<br>$AGU_{11}$ | C<br>$C_{22}GA$ | T<br>$C_{23}GT$ | C<br>$GGC_{24}$ | T<br>$GGU_{12}$ | C<br>$U_{15}GC$ | T<br>$U_{16}GT$ |
| T | A<br>$AU_{17}A$ | G<br>$AU_{18}G$ | A<br>$C_{25}TA$ | G<br>$C_{26}TG$ | A<br>$GU_{21}A$ | G<br>$GU_{22}T$ | A<br>$U_{25}TA$ | G<br>$U_{26}TG$ |
|   | C<br>$AU_{19}C$ | T<br>$AU_{20}T$ | C<br>$C_{27}TC$ | T<br>$C_{28}TT$ | C<br>$GU_{23}C$ | T<br>$GU_{24}T$ | C<br>$U_{27}TC$ | T<br>$U_{28}TT$ |

In addition, also when the modified nucleotide n-mer is that of tetramer or higher (n≧4) nucleotide, the translation is carried out in the same way, for example, on the basis of the relation table prepared by relating at least 1 kind of $4^n$ kinds of nucleotide n-mers (n≧4), which are represented in the relation table prepared by the one-to-one combination of 4 kinds of nucleosides, to 1 kind of the modified nucleotide n-mer (n≧4).

The functional molecule according to the present invention obtained by the process for producing the functional molecule according to the present invention has the affinity and specificity comparable to those of the antibody and can be preferably and widely used for various fields. For instance, the functional molecule according to the present invention, which was found as the functional molecule having an affinity to a specific protein and produced by the producing method of the functional molecule according to the present invention, can be preferably used in fields of drugs and drug delivery. Further, the functional molecule according to the present invention, which was found as the functional molecule having an affinity to a specific DNA sequence and produced by the producing method of the functional molecule according to the present invention, can be preferably used for conquering a disease caused by gene abnormality and discovering a function of a protein into which a gene is translated. In addition, the functional molecule according to the present invention, which was found as the functional molecule having an affinity to the molecule prepared by mixing a reaction intermediate and produced by the producing method of the functional molecule according to the present invention, can be preferably used for development of a catalyst for efficient progress of the reaction.

Examples of the present invention will be described as follows. However, the present invention is not restricted by these examples.

EXAMPLE 1

In the way shown in FIGS. 3A to 3D, producing (synthesis and identification) the functional molecule having an affinity to a specific protein was operated. Specifically, first, by the process expressed by the following formula, 6 kinds of deoxycytidine relatives ($C_{1-6}$) having a functional group at the 5th position of cytosine and 6 kinds of deoxyuridine relatives ($U_{1-6}$) having a functional group at the 5th position of uracil were each synthesized (prepared).

Next, each of the synthesized (prepared) 12 kinds of the modified nucleoside dimer was one-to-one related to any one selected from 16 patterns of the relation table represented in the following Table 1. The relation table was prepared by combining one-to-one the 4 nucleosides composing the DNA.

TABLE 1 relation table

| 3' | 5' | | | |
|---|---|---|---|---|
|  | A | C | G | T |
| A |  | $C_2A$ |  | $U_3A$ |
| C | $AC_1$ | $C_3C$ | $GC_6$ | $U_4C$ |
| G |  | $C_4G$ |  | $U_5G$ |
| T | $AU_1$ | $C_5T$ | $GU_2$ | $U_6T$ |

Next, by the phosphoroamidite method, 12 kinds of the modified oligonucleotide amidite (M) represented in the relation table in the above Table 1 were chemically synthesized. Practically, for instance, the modified nucleotide dimer ($AU_1$) can be, as shown in the following formula, synthesized from deoxyadenosine and modified deoxyuridine.

deoxyadnosine modified deoxyuridine ($U_1$)

phosphoamidite (AU₁)

Where, DMTr in the formula represents a dimethoxytrityl group.

And, by using a DNA synthesizer as shown in FIG. 2, a random polymer pool was prepared containing random oligonucleotide $N_{20}$-$M_{20}$-$N_{20}$ (DNA 80-mer) consisting of a fixed oligonucleotide sequence 20-mer ($N_{20}$)—a modified oligonucleotide random sequence 20-mer ($M_{20}$)—the fixed oligonucleotide sequence 20-mer ($N_{20}$). The above described step is the producing step.

Next, by using this random polymer pool (FIG. 3A), the modified oligonucleotide sequence (functional molecule), which was bound strongly with the specific protein, was identified. An open square in FIG. 3A expresses the fixed nucleotide sequence and a wavy line expresses the modified nucleotide random sequence.

First, an affinity column, which was filled with beads bound with human albumin as the target, was prepared and a solution containing the random polymer pool was passed through this column to leave at a specific condition and, then, the modified oligonucleotide sequence showing the affinity to the target adsorbed to the column (FIG. 3B). Subsequently, remained components other than the remained oligonucleotide sequence were removed by washing sufficiently with a buffer solution and the solution containing human albumin was passed through the column to select and collect the oligonucleotide containing the modified oligonucleotide random sequence (FIG. 3C). The step described above is the selecting step.

This selected modified oligonucleotide sequence was amplified by PCR followed by cloning to know the base sequence of the DNA. As the result, a portion of the base sequence of the determined modified oligonucleotide was "ATGCTCTAGCCCCT" (SEQ ID NO: 1) (FIG. 3D). The step described above is the determining step.

Translating this base sequence on the basis of the relation table presented "$AU_1GC_6U_4CU_3AGC_6C_3CC_5T$" resulting in identification of a structure of the functional molecule (FIG. 3D). The step described above is the translating step.

It was found that the functional molecule obtained was bound specifically with human albumin to work similarly to the antibody.

EXAMPLE 2

As a random polymer pool containing the modified oligonucleotide sequence, a 5'-$^{32}$P radiolabeled standard (that prepared by previously labeling a nucleotide monomer containing a modified base by a radioactive element) of the DNA random pool (total amount 20 OD) [nucleotide fixed sequence 20-mer DNA ($N_{20}$)] synthesized in Example 1 was prepared.

The step described above is the step of producing the modified oligonucleotide sequence.

On the other hand, a cytoplasm fraction was purified from a rat liver tissue in the usual manner. A protein mixture contained in this fraction was subjected to linear isoelectric focusing (pH 4 to 7) in the usual manner followed by SDS-PAGE as two-dimensional electrophoresis. Following the electrophoresis, the protein contained in the protein mixture was blotted on a nitrocellulose membrane by the western blotting method.

The nitrocellulose membrane, on which the protein mixture was immobilized, was soaked in a diluted solution of $N_{20}M_{20}N_{20}$ (DNA 80-mer), which was the random polymer pool containing this radiolabeled modified oligonucleotide sequence, to shake for 1 hour. Thereafter, this nitrocellulose membrane was washed with the buffer solution to remove nonspecific remains and a position (the position to which the radiolabeled modified oligonucleotide was strongly bound), where strong radioactivity was observed, of the nitrocellulose membrane was identified by using an X-ray film.

30 positions, where strong radioactivity was observed, of the nitrocellulose membrane were cut to apply a voltage in an ionic solution (3M Na acetate, pH 4.80, 0.1% bromophenol blue solution) for collection of the modified oligonucleotide by electroelution. Following observation of radioactivity of each solution, the DNA was amplified by the PCR method using a complementary chain of a fixed sequence as the primer. Individual PCR products were subjected to acrylamide gel electrophoresis. As a result, distinct bands of 28 kinds of the modified oligonucleotide sequences were observed. The step described above is the selecting step.

The obtained 28 kinds of the modified oligonucleotide sequences were each subjected to cloning by using plasmid vectors to determine the DNA sequences. The step described above is the determining step. Following this step, the sequence of the modified DNA was determined by the same manner as described in Example 1 to synthesize the modified DNA (the functional molecule) by employing an automated DNA synthesizer. The step described above is the translating step.

It was observed that the obtained modified DNA could recognize the protein isolated by two-dimensional electrophoresis specifically. Further, the dissociation constant of an available protein was measured by applying a surface plasmon resonance method and, as the result, was $1.0 \times 10^{-7}$ to $1.0 \times 10^{-9}$ and the protein was found to have the affinity.

The same effect was obtained in the case where native electrophoresis, which was replaced to the SDS-PAGE, as the second dimensional electrophoresis was applied to isolate the protein keeping its molecular structure.

In Example 2, a radiolabeled random polymer pool was used. In addition to the radioisotope, labeling material can be suitably selected from labeling materials such as enzymes, fluorescent materials and chemiluminescence materials. In addition, a transferred proteins on a support such as a blotted nitrocellulose membrane for a transferring operation can be visualized by staining or spectroscopy to extract a DNA sequence from a portion having an abundant transferred proteins for cloning and sequencing.

What is claimed is:

1. A process for producing a functional molecule having an affinity to a target, comprising:
   a forming step which forms a modified nucleotide n-mer (where, n represents an integer) containing a modified nucleoside prepared by introducing a substituent into a nucleoside composing a nucleic acid;
   a producing step which produces a modified oligonucleotide sequence by randomly polymerizing the modified nucleotide n-mer;
   a selecting step which selects a sequence having an affinity to a target from the modified oligonucleotide sequences;
   a determining step which amplifies the selected modified oligonucleotide sequence and determines the base sequence thereof; and
   a translating step which translates the sequence of the modified oligonucleotide sequence, of which base sequence has been determined, on the basis of a correspondence relation,
   wherein the correspondence relation relates at least one of $4^n$ kinds of nucleotide n-mers, which are presented in the correspondence relation prepared by one-to-one combination of 4 kinds of nucleosides, to a modified nucleotide n-mer.

2. A process for producing the functional molecule according to claim 1, wherein the producing step prepares the modified oligonucleotide sequence and prepares a random polymer pool containing the modified oligonucleotide sequence.

3. A process for producing the functional molecule according to claim 1, wherein the nucleic acid is one of a DNA and an RNA.

4. A process for producing the functional molecule according to claim 1, wherein the number of the modified nucleotide n-mer is 5 to $4^n$.

5. A process for producing the functional molecule according to claim 1, wherein the modified nucleotide n-mer is a modified nucleotide dimer
   wherein the number of the modified nucleotide dimer is 5 to 16.

6. A process for producing the functional molecule according to claim 1, wherein the modified nucleotide n-mer is a modified nucleotide trimer
   wherein the number of the modified nucleotide trimer is 5 to 56.

7. A process for producing the functional molecule according to claim 1, wherein the substituent is introduced into a 5th position of a pyrimidine base of the nucleoside.

8. A process for producing the functional molecule according to claim 1, wherein the substituent is selected from groups represented by the following structural formula (I):

structural formula (I)

where, in the formula (I), R represents any one of groups selected from one of natural and nonnatural amino acids, metal complexes, fluorescent dyes, oxidation-reduction pigments, spin label compounds, hydrogen atom, alkyl groups having carbon number ranging from 1 to 10, and groups selected from the following formulae (1) to (10); P represents the pyrimidine base 9. A process for producing the functional molecule according to claim 1, wherein the modified nucleotide n-mer is a modified oligonucleotide amidite.

10. A process for producing the functional molecule according to claim 1, wherein the modified oligonucleotide sequence is synthesized by using a DNA synthesizer.

11. A process for producing the functional molecule according to claim 1, wherein the modified oligonucleotide sequence is synthesized by annealing a nucleotide monomer to a nucleotide random sequence and ligating the nucleotide monomer by using at least one of a DNA ligase and an RNA ligase.

12. A process for producing the functional molecule according to claim 1, wherein the modified oligonucleotide sequence has a fixed oligonucleotide sequence on both terminals thereof.

13. A process for producing the functional molecule according to claim 1, wherein the selecting step is carried out by affinity chromatography employing a column in which beads bound with a target is filled.

14. A process for producing the functional molecule according to claim 1, wherein the selecting step is carried out by dissociating the modified oligonucleotide from the target through monitoring a dissociation constant of the target and the modified oligonucleotide sequence.

15. A process for producing the functional molecule according to claim 1, wherein the selecting step is carried out by the manner in which 2 or more targets are immobilized on a matrix having a linear to cubic spatial arrangement, a random polymer pool containing the modified oligonucleotide sequence is worked on the matrix on which the target has been immobilized, and then, a modified oligonucleotide sequence attached to the target is purified.

16. A process for producing the functional molecule according to claim 15, wherein the immobilization on the matrix is carried out by any one selected from a western blotting method, dot blotting method, and slot blotting method.

17. A process for producing the functional molecule according to claim 15, wherein the target immobilized on the matrix is labeled with at least one of labeling materials selected from a radioisotope, chemiluminescence materials, fluorescent materials, enzymes, antibodies, ligands and receptors.

18. A process for producing the functional molecule according to claim 14, wherein the modified oligonucleotide sequence contained in the random polymer pool is labeled with at least one of labeling materials selected from radioisotopes, chemiluminescence materials, fluorescent materials, enzymes, antibodies, ligands and receptors.

19. A process for producing the functional molecule according to claim 14, wherein the selecting step is carried out by cutting the modified oligonucleotide sequence, which has been bound to the target immobilized on the matrix, together with the matrix to yield a cut piece and, then, one of directly conducting PCR and collecting the modified oligonucleotide sequence from the cut piece.

20. A process for producing the functional molecule according to claim 19, wherein the collection of the modified oligonucleotide sequence from the cut piece is carried out by one of the electroelution method applying a voltage using an ionic solution and a method using a hot water.

21. A process for producing the functional molecule according to claim 1, wherein the target is at least one selected from proteins, lipoproteins, sugar proteins, polypeptides, lipids, polysaccharides, lipopolysaccharides, nucleic acids, environmental hormones, drugs, and a complex of these substances.

22. A process for producing the functional molecule according to claim 1, wherein the amplification step is carried out by any one method selected from a PCR method, LCR method, 3SR method, SDA method, RT-PCR method, ICAN method and LAMP method, and the base sequence is determined by cloning.

23. A process for producing the functional molecule according to claim 1, wherein the translating step is carried out for every n base from the 5' terminal side of the modified oligonucleotide sequence on the basis of the correspondence relation, and wherein the modified oligonucleotide sequence is made by polymerizing randomly a modified nucleotide n-mer and the base sequence of the modified oligonucleotide sequence has been determined.

24. A process for producing the functional molecule according to claim 23, wherein the modified nucleotide n-mer is a modified nucleotide dimer and the translating step is carried out for every 2 base from the 5' terminal side of the modified oligonucleotide sequence on the basis of the correspondence relation, and wherein the modified oligonucleotide sequence is made by randomly polymerizing a modified nucleotide dimer and the base sequence of the modified oligonucleotide sequence has been determined.

25. A process for producing the functional molecule according to claim 23, wherein the modified nucleotide n-mer is a modified nucleotide trimer and the translating step is carried out for every 3 base from the 5' terminal side of the modified oligonucleotide sequence on the basis of the correspondence relation, and wherein the modified oligonucleotide sequence is made by randomly polymerizing a modified nucleotide trimer and the base sequence of the modified oligonucleotide sequence has been determined.

* * * * *

SEQUENCE LISTING

<160> NUMBER OF SEQ ID NOS: 1

<210> SEQ ID NO 1
<211> LENGTH: 14
<212> TYPE: DNA
<213> ORGANISM: Artificial Sequence
<220> FEATURE:
<223> OTHER INFORMATION: Description of Artificial Sequence:DNA for
      manufacturing a derivative which may bond to human
      albumin

<400> SEQUENCE: 1
atgctctagc ccct                                                     14